United States Patent [19]

Al-Saleh

[11] Patent Number: 5,620,429
[45] Date of Patent: Apr. 15, 1997

[54] FEMININE NAPKIN ALLOWS EXTERNAL SEXUAL INTERCOURSE

[76] Inventor: Abdul A. A. Al-Saleh, P.O. Box 21952, Riyadh 11485, Saudi Arabia

[21] Appl. No.: 493,795

[22] Filed: Jun. 22, 1995

[51] Int. Cl.⁶ .............................. A61F 13/15; A61F 5/453
[52] U.S. Cl. .................. 604/385.1; 604/387; 600/38; 600/41
[58] Field of Search .................. 604/385.1, 387; 600/38, 41; 128/830, 835, 883, 918

[56] References Cited

U.S. PATENT DOCUMENTS

| | | | |
|---|---|---|---|
| 3,769,979 | 11/1973 | Freney | 604/387 |
| 4,072,151 | 2/1978 | Levine | 604/387 |
| 4,182,336 | 1/1980 | Black | 604/387 |
| 4,605,403 | 8/1986 | Tucker | 604/385.1 |
| 5,413,117 | 5/1995 | Wills | 128/830 |

*Primary Examiner*—Robert A. H. Clarke
*Attorney, Agent, or Firm*—David M. Klein; Bryan Cave LLP

[57] ABSTRACT

A feminine napkin that allows that permits external sexual intercourse. A round bag is attached to the front side of the napkin. The bag is in the size and shape of the vagina to give the husband the same sexual feelings. The round bag has an opening and rings, windings and protrusions, as well as a suitable cream. This bag has also a downward extension for fixing the napkin on the vagina opening when the woman lies on her back. The fixing extension is placed between the rumps and may be coated by an adhesive material. The round bag can be taken off the napkin and disposed while continuing to use the napkin.

21 Claims, 7 Drawing Sheets

FEMININE NAPKIN ALLOWS EXTERNAL SEXUAL INTERCOURSE

FIELD OF THE INVENTION

This invention relates to a feminine napkin that allows the husband to engage in a sexual encounter externally and to have sexual enjoyment without inserting his penis into a woman's vagina during the days in which the woman uses feminine napkins.

BACKGROUND OF THE INVENTION

There are times in which the husband cannot engage in a sexual encounter with his wife, for example, when she is in the menses period, having continuous bleeding from her womb, during the period following delivery, when she suffers from vaginitis or a womb ulceration which may become more serious if she engages in a sexual encounter, when there is fear of transfer of infection between the two parties, or in other situations in which a doctor forbids sexual intercourse between the husband and his wife. This also can occur when the woman uses the rhythm method to prevent pregnancy without using contraceptives so that sexual relations are stopped for certain days, or when the woman cannot satisfy the excessive desire of her husband for sex.

As a result, the wife suffers from the feeling of depression since she cannot satisfy her husband's sexual desire, and also results in the husband becoming nervous and frustrated for he cannot satisfy his sexual desire. This causes some husbands to the use isolators and to engage in sexual relations during menses, which may result in infections to the wife. Some husbands may also seek sexual enjoyment from other sources, which affects family relations and raises the possibility of transferring sexual diseases. Many divorce cases and familial disputes occur during the periods when couples are forced to stop love making.

SUMMARY OF THE INVENTION

The present invention makes it possible to maintain the continuity of the love relationship between the husband and his wife without compulsory interruption of sexual relations so that the wife can give her husband full sexual enjoyment at any time he wishes, during menses, continuous bleeding, vulvitises or any diseases that prevents sexual relations without causing any injury or suffering to the wife. This strengthens the relationship between the family members for there will be no compulsory love making cessation, which will minimize cases of divorce, quarrels and family disputes which may occur during the period in which love making ceases.

The present invention enables a sexual encounter to occur without taking off the feminine napkin and without inserting the penis into the vagina. This is achieved by attaching a circular bag to the feminine napkin from the outside. This circular bag is designed to play the role of the vagina during sexual intercourse. The husband can insert his penis into the circular bag while his wife is lying on her back with the napkin in its location without putting on a short. The napkin is fixed between the thighs and fixed from behind by an extending portion that is placed between the rumps. The opening of the circular bag is designed in the shape of the female vagina with all of its details including the hymen. The circular bag is made of a soft material including rings, windings and protrusions from inside as well as a suitable cream to give the husband the maximum sexual enjoyment possible.

When it becomes impossible to engage in a sexual encounter with the wife from the front side, such as when she is pregnant, a circular bag can be used for engaging in sex from the back side while the woman is lying on her side. For this purpose, a circular bag that is opened from the back can be used.

DETAILED DESCRIPTION OF THE PREFERRED EMBODMENT

Figure 1:
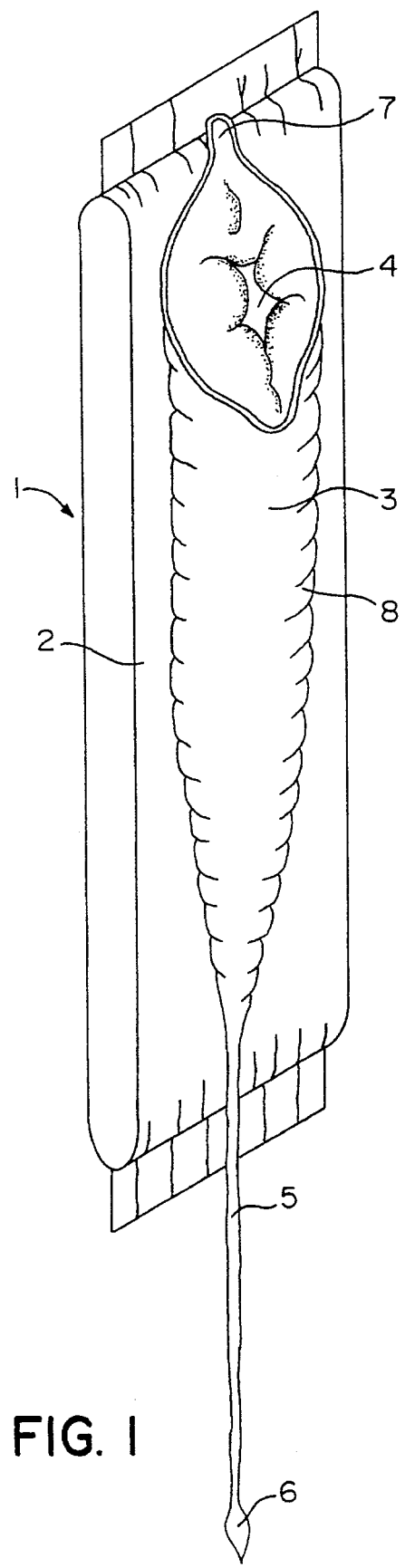
FIG. 1 is a perspective view of the feminine napkin that allows external sexual intercourse in accordance with the present invention. A circular bag appears attached to the napkin on the front side which plays the role of the vagina and allows the husband to insert himself into it.

FIG. 1 shows a feminine napkin 1 having a front side 2. A circular bag 3 that has an opening 4 at the upper side, is stuck to front side 2. Insertion occurs through opening 4. Bag 3 plays the role of the vagina during sexual intercourse. Insertion is performed in that bag 3 gives the man the same sexual feelings. The circular bag 3 has a downward extension 5 that works as a fixing side for fixing the napkin 1 to the vagina opening when the woman lies on her back without wearing panties. The fixing part 5 is preferably placed between the rumps with a suitable sticky material on it. The napkin is preferably fixed from the front side by pressing it between the thighs while the legs are stretched and the circular bag 3 opening 4 is directed upward to allow the husband to insert into the circular bag 3 through the opening 4 while positioned opposite the wife. When the weather is cold the circular bag can be exposed to a hot air stream from a hair dryer before using the bag directly.

Medically there will be no injury to the woman if she is subject to sexual excitement during menses because there is no insertion of the penis into the vagina.

Figure 2:
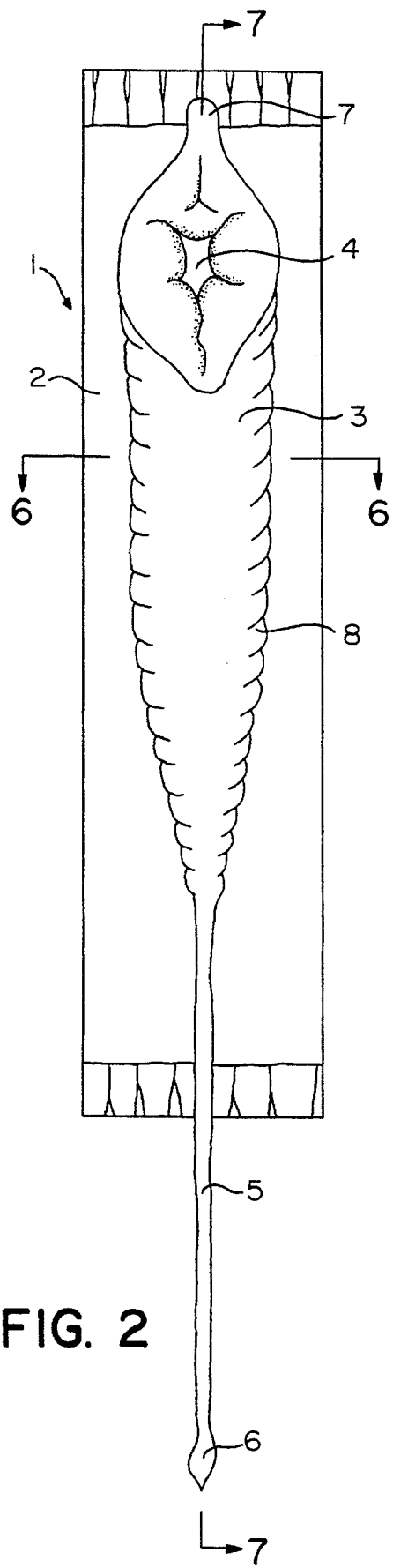
FIG. 2 is a front view of the feminine napkin that allows external sexual encounter as shown in FIG. 1. A downwardly extending portion acts as a sticky fixing part to be placed between the rumps in order to fix the napkin to the vagina opening while the woman is lying on her back without wearing panties.

FIG. 2 shows a front view of the napkin 1 and the circular bag 3. The opening 4 of the bag 3 is shaped like a woman's vulva with all of its components, including the labia minora, labia majora, clitoris and hymen, in the same natural color of the body.

Figure 3:
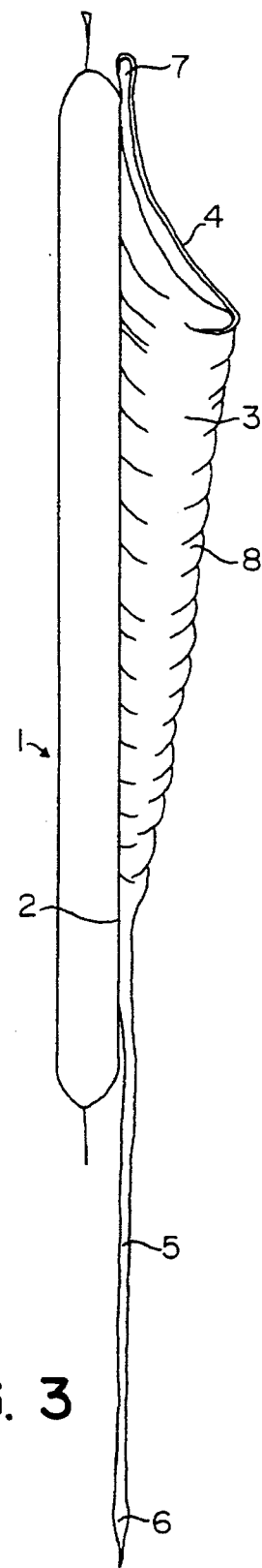
FIG. 3 is a side view of the napkin that allows external sexual encounter as shown in FIG. 1. The bag attached to the napkin has a free edge on its upper side and it is not attached to the napkin. This facilitates pulling the bag off the napkin to continue to use the napkin to save cost.
Figure 4:
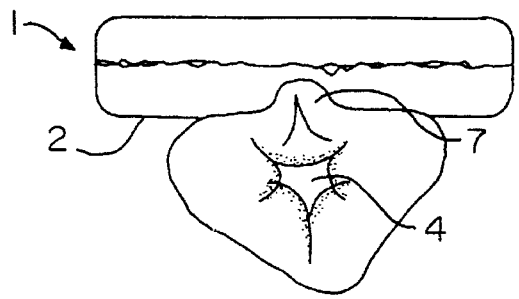
FIG. 4 is a top view of a napkin that allows external sexual intercourse before use as shown in FIG. 1.
Figure 5:
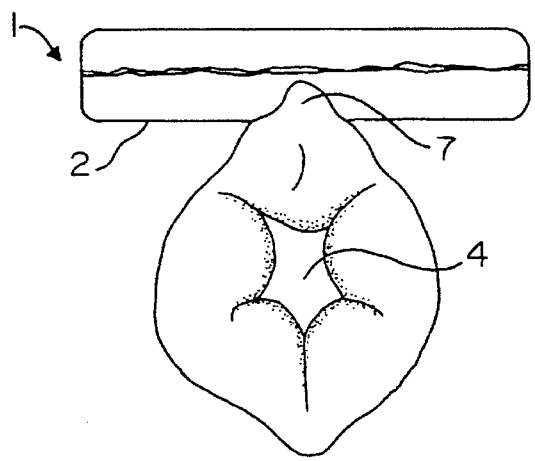
FIG. 5 is a top view of napkin that allows external sexual intercourse as shown in FIG. 1. This view shows the shape of the bag during use.
Figure 6:
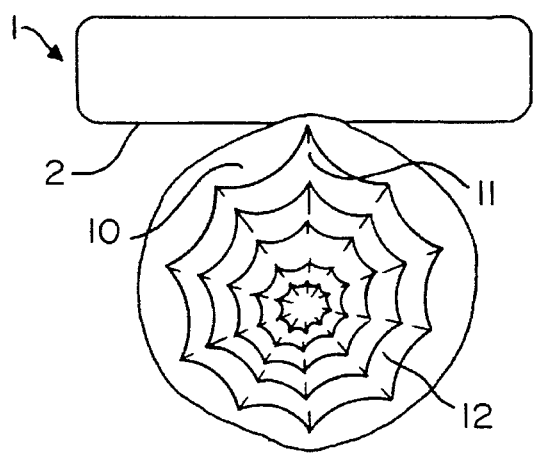
FIG. 6 is a cross sectional view through Sec. 6—6 of FIG. 2. This figure shows the rings, windings and inside protrusions in the bag that helps to give the husband as full enjoyment as possible with the use of a suitable cream.
Figure 7:
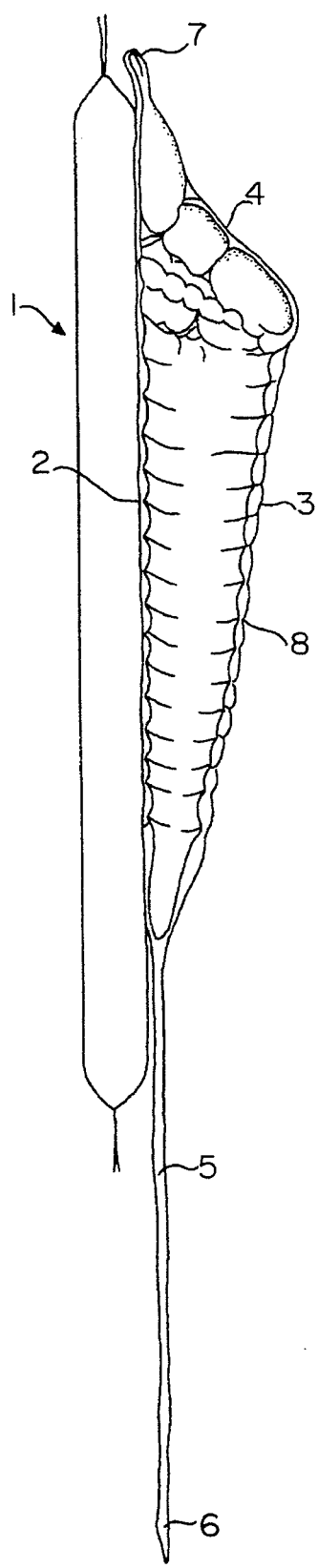
FIG. 7 is a cross-sectional view through Sec. 7—7 FIG. 2 showing the insertion opening which can include a hymen, and also showing the rings, windings and protrusions inside the circular bag.

FIG. 3 shows a side view of the napkin 1. The upper part 7 of the opening 4 is loose to facilitate taking the bag 3 off the napkin 1 and disposing it while continuing to use the napkin 1 for cost savings. That napkin 1 is usually put on immediately before a sexual encounter. The circular bag 3 is made up of a flexible soft material. It contains rings 8 (FIG. 2), windings 12 (FIG.6), and protrusions from the inside to give the husband the maximum possible sexual enjoyment with a suitable cream inside the circular bag. To facilitate opening the entrance 4, the opening 4 has fine extensions 9 on both sides so that they can be held open. This also makes it easy to put an adhesive tape on the opening to keep it clean and to save the cream inside from becoming dry. To keep the circular bag 3 in a straight shape and to keep it from becoming pressed down during use, the thickness of surface 10 (FIG. 6) attached to the napkin is increased. An inside isolator or engraved line 11 (FIG. 6) is preferably placed in the middle of the surface of the side of the bag adhered to the napkin so as not to let the extra thickness prevent folding the napkin between the woman's thighs.

Figure 8:
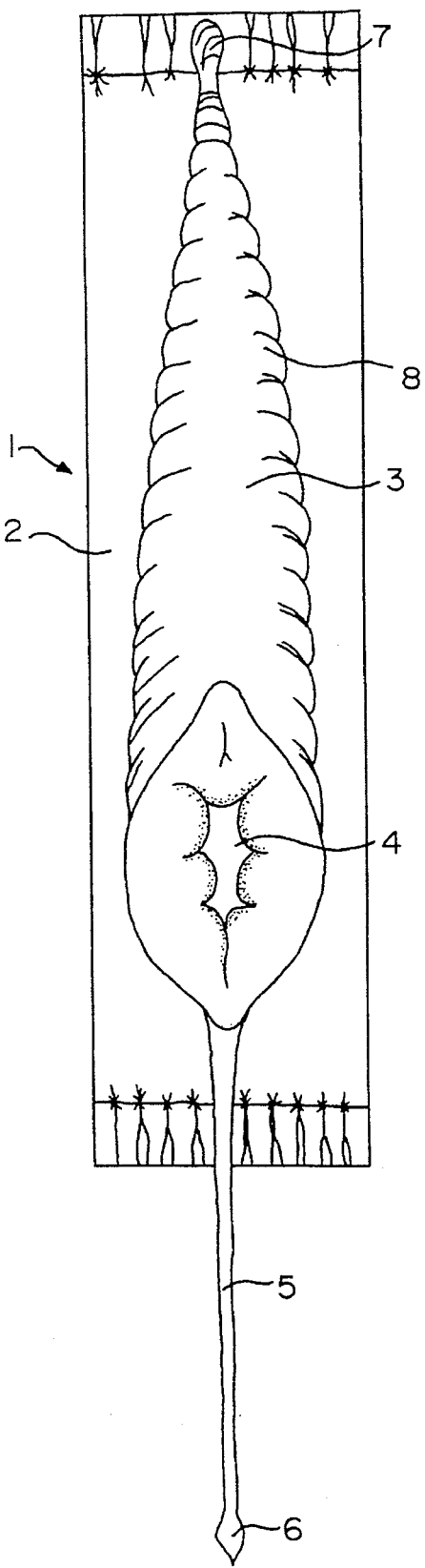
FIG. 8 is a front view of a feminine napkin that allows an external sexual intercourse in accordance with the present invention. The opening of the circular bag is toward the button for enabling sexual intercourse from the back.

FIG. 8 shows an alternative embodiment of a feminine napkin that allows sexual encounter from the back when it is not possible or practical to practice sexual intercourse from the front, especially when the wife is pregnant. In this embodiment, the bag opening is at the bottom side. In practice, the woman lies on her side and insertion is practiced in the circular bag 3 as discussed above.

Figure 9:
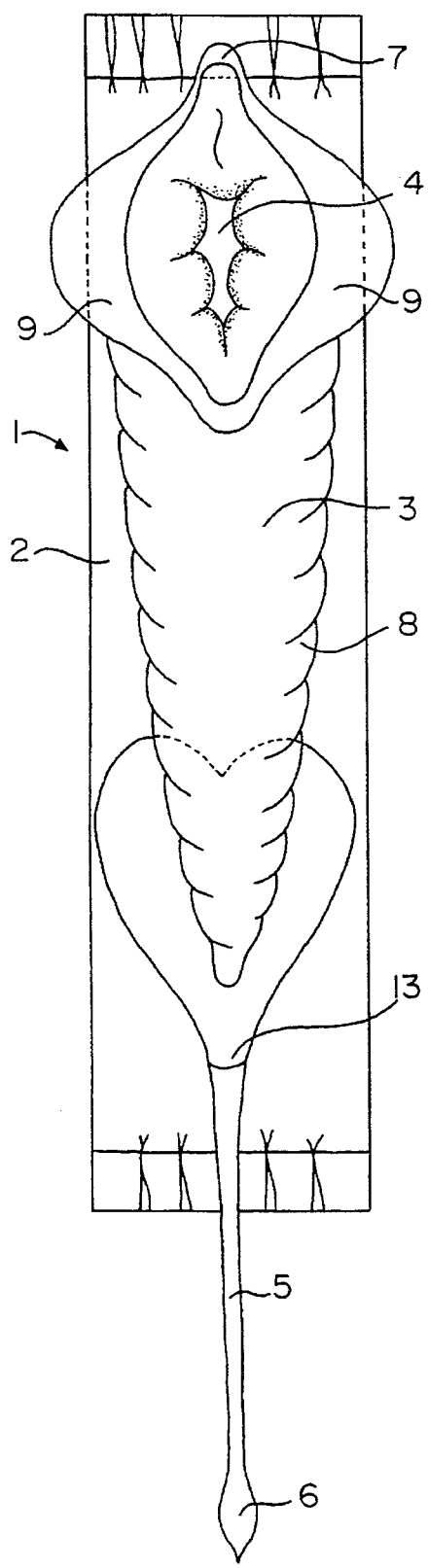
FIG. 9 is a front view for a feminine napkin that allows an external sexual encounter in accordance with the present invention. The insertion opening has side extension to be held with and open the bag, and small extensions on the other sides to facilitate sealing the cover of the opening. The fixing side at the bottom of the circular bag is separated from the bag. This makes it is possible to take off the bag and to turn it over to make the opening be at the bottom side. A sign or indicia is provided on the fixing side to show the location of sticking the bag when it is turned over.

FIG. 9 shows circular bag 3 which is separate from the fixing edge 5 to make it possible for the bag to the pulled off and reattached after turning it down so that opening 4 is in a downward position.

Figure 10:
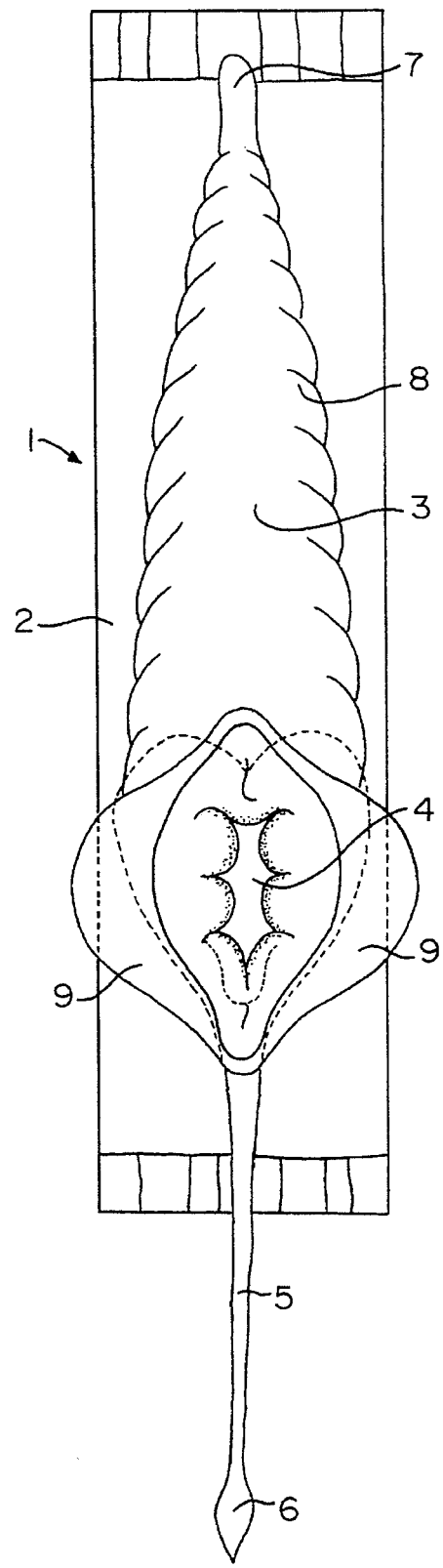
FIG. 10 is a front view of the napkin shown in FIG. 9 after turning over the bag and affixing it with the opening on the bottom for use in back insertion.
Figure 11:
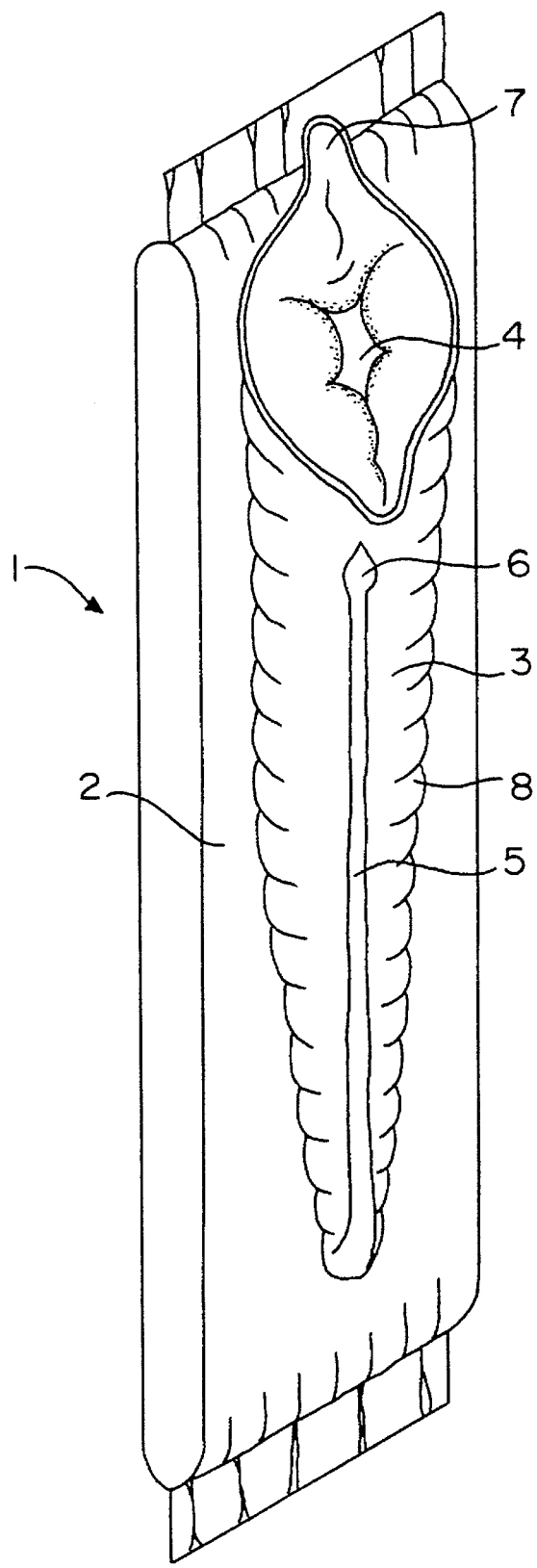
FIG. 11 shows the napkin during packaging at which time the fixing part 5 is stuck to bag 3.

FIG. 10 shows the napkin of FIG. 9 after pulling off the circular bag 3 and reattaching it with the opening 4 in the downward position by placing the top end 7 on the sign 13. The napkin according to this invention can be used in many other situations that will be appreciated by those skilled in the art. For example, the fixing tape can be folded up and an adhesive tape can be placed on all the napkin.

Figure 12:
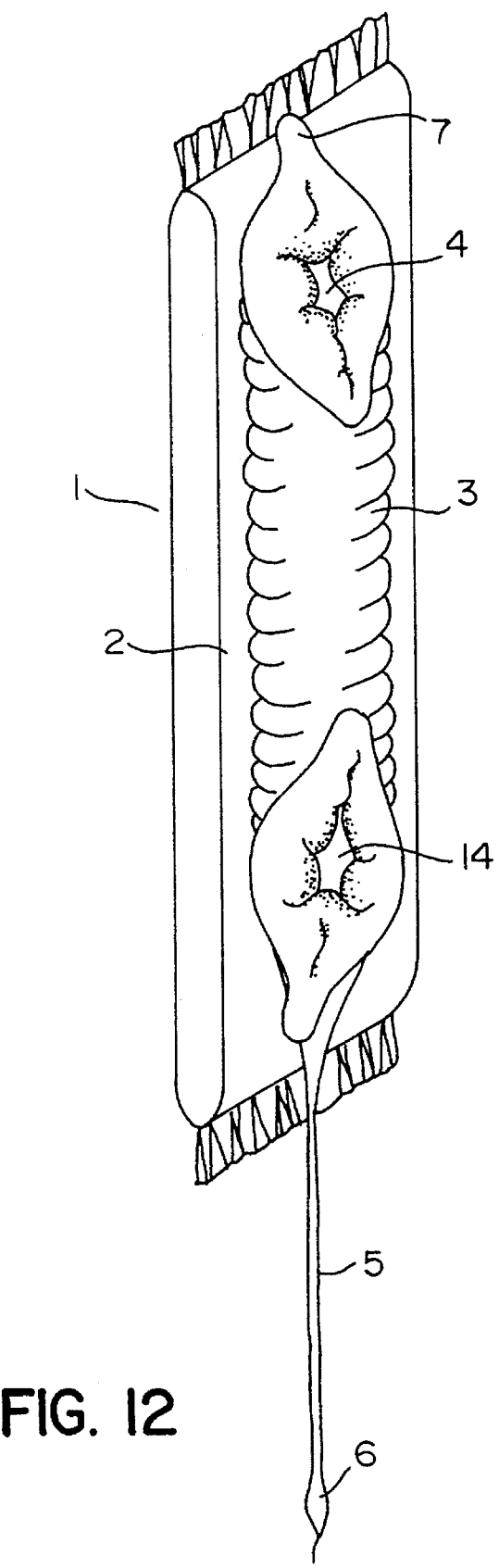
FIG. 12 is a perspective view of a feminine napkin in accordance with the present invention in which the outer bag has two ends, wherein each end is suitable for enabling insertion of a penis therein.

FIG. 12 shows an alternative embodiment of a feminine napkin wherein the outer bag has two open ends 4 and 14. Each end is suitable for enabling insertion of a penis therein, whereby the outer bag simulates a vagina and may be used from the front or the rear.

Although the present invention has been described in detail with respect to certain embodiments and examples, variations and modifications exist which are within the scope of the present invention as defined in the following claims.

I claim:

1. An apparatus for simulating sexual intercourse which comprises in combination:

a feminine napkin having a first side for being positioned facing and adjacent to a woman's vagina, and a second side;

a vagina simulating outer bag means being attached to the second side of the napkin, the vagina simulating outer bag means comprising at least one open end for insertion of a penis therein when the napkin is in use, the vagina simulating outer bag means simulating a vagina; and means for securing the napkin to the woman adjacent to the vagina during use of the napkin and the vagina simulating outer bag means.

2. The apparatus according to claim 1 wherein the vagina simulating outer bag means is constructed of a soft flexible material.

3. The apparatus according to claim 1 wherein the inside of the vaginas simulating outer bag means comprises a sensitivity enhancing surface selected from the group consisting of rings, windings and protrusions.

4. The apparatus according to claim 1 further comprising a lubricating cream located inside the vagina simulating outer bag means.

5. The apparatus according to claim 1 wherein the means for securing comprises a downwardly extending fixing edge secured to the napkin, the fixing edge adapted to be secured between the woman's rumps in order to fix the position of the napkin.

6. The apparatus according to claim 5 wherein the fixing edge is at least partially coated by an adhesive material.

7. The apparatus according to claim 5 wherein an end of the fixing edge is not coated by the adhesive to facilitate removal of the napkin.

8. The apparatus according to claim 5 wherein the fixing edge is removably attached to the napkin.

9. The apparatus according to claim 5 wherein the fixing edge is integral with the vagina simulating outer bag means.

10. The apparatus according to claim 1 wherein the open end of the vagina simulating outer bag means is shaped and colored like a woman's vagina.

11. The apparatus according to claim 1 further comprising adhesive for affixing the vagina simulating outer bag means to the napkin.

12. The apparatus according to claim 1 wherein the vagina simulating outer bag means is removably attached to the napkin.

13. The apparatus according to claim 12 wherein an upper edge of the vagina simulating outer bag means is not affixed to the napkin to facilitate removal of the vagina simulating outer bag means from the napkin.

14. The apparatus according to claim 1 wherein the vagina simulating outer bag means further comprises lateral extensions adjacent to the opening to facilitate opening of the vagina simulating outer bag means.

15. The apparatus according to claim 1 wherein the vagina simulating outer bag means further comprises at least one lateral extension adjacent to the opening to facilitate sealing the opening.

16. The apparatus according to claim 1 wherein a portion of the vagina simulating outer bag means adjacent to the napkin has an increased thickness.

17. The apparatus according to claim 16 further comprising a vertical isolator along the thicker portion of the outer bag to facilitate folding the napkin between the woman's thighs.

18. The apparatus according to claim 1 wherein the vagina simulating outer bag means opening is located toward the bottom side of the napkin to be used for rearward insertion.

19. The apparatus according to claim 1 wherein the opening of the vagina simulating outer bag means is openably sealed by an adhesive material.

20. The apparatus according to claim 1 further comprising indicia means for positioning the napkin, the vagina simulating outer bag means, and the securing means in correct relationship.

21. The apparatus according to claim 1 wherein the vagina simulating outer bag means has two ends, and wherein each end is open for enabling insertion of a penis into either open end whereby the vagina simulating outer bag means simulates a vagina and may be used from the front or the rear.

* * * * *